(12) United States Patent
Imre et al.

(10) Patent No.: US 9,063,083 B2
(45) Date of Patent: Jun. 23, 2015

(54) METHOD AND SENSOR DEVICE FOR MEASURING A CARBON DIOXIDE CONTENT IN A FLUID

(71) Applicant: Anton Paar GmbH, Graz-Strassgang (AT)

(72) Inventors: Michael Imre, Graz (AT); Johann Loder, Weiz (AT); Gerhard Pfeifer, Gratkorn (AT)

(73) Assignee: Anton Paar GmbH, Graz-Strassgang (AT)

( * ) Notice: Subject to any disclaimer, the term of this patent is extended or adjusted under 35 U.S.C. 154(b) by 0 days.

(21) Appl. No.: 13/724,776

(22) Filed: Dec. 21, 2012

(65) Prior Publication Data

US 2014/0160480 A1 Jun. 12, 2014

(30) Foreign Application Priority Data

Dec. 23, 2011 (AT) .................................. A 1884/2011

(51) Int. Cl.
*G01N 21/55* (2014.01)
*G01N 21/552* (2014.01)
*G01N 21/27* (2006.01)

(52) U.S. Cl.
CPC .............. *G01N 21/55* (2013.01); *G01N 21/274* (2013.01); *G01N 21/552* (2013.01)

(58) Field of Classification Search
CPC . G01N 21/553; G01N 21/552; G01N 21/648; G01N 21/35; A61B 5/14514; A61B 5/14532; A61B 5/1459
USPC ................. 356/445, 432, 434–436, 440, 442; 422/82.05, 68.1; 250/340, 353
See application file for complete search history.

(56) References Cited

U.S. PATENT DOCUMENTS 5,701,008 A * 12/1997 Ray et al. ...................... 250/352

* cited by examiner

*Primary Examiner* — Tri T Ton
(74) *Attorney, Agent, or Firm* — Laurence A. Greenberg; Werner H. Stemer; Ralph E. Locher

(57) ABSTRACT

An ATR sensor has a housing and sensor components in the housing including an electromagnetic radiation source for emitting a predefined wavelength range, a reflection body permeable for radiation and contactable with a fluid to be evaluated, and a detector for the reflected radiation as well as other members for conducting the measurement and for operation. The sensor is particularly suited for measuring a $CO_2$ content of a fluid. Before sealing the housing in a gas-tight manner, in particular for avoiding a measurement value drift and for keeping the radiation paths free of $CO_2$, a $CO_2$ getter material is introduced into the housing and/or into a receiving space of an additional housing that communicates with the interior space of the housing before sealing the interior space and/or the receiving space.

17 Claims, 2 Drawing Sheets

METHOD AND SENSOR DEVICE FOR MEASURING A CARBON DIOXIDE CONTENT IN A FLUID

CROSS-REFERENCE TO RELATED APPLICATION

This application claims the priority, under 35 U.S.C. §119, of Austrian patent application A 1884/2011, filed Dec. 23, 2011; the prior application is herewith incorporated by reference in its entirety.

BACKGROUND OF THE INVENTION

Field of the Invention

The invention relates to an ATR sensor and to a method for measuring the $CO_2$ content of fluids by way of the ATR sensor. The ATR sensor has, within a housing, the following sensor components: an electromagnetic source of radiation for emitting a predefined wavelength range, a reflection body permeable for radiation and contactable with the fluid to be evaluated, and a detector for the reflected radiation as well as other members for conducting the measurement and for operation.

The invention is for measuring the $CO_2$ content of fluids, wherein the fluids can consist of multiple components. In particular, liquids, such as beverages, that are made up of multiple components can be evaluated in this manner. Mostly it is difficult to measure the $CO_2$ contained in fluids, as $CO_2$ is an inert gas. One way of measuring $CO_2$ is the so-called ATR method (Attenuated Total Reflection).

The technique of measuring $CO_2$ via attenuated total reflection, also known by the designation of multiple internal reflection, has been used for $CO_2$ analysis for many years. ATR spectroscopy utilizes the effect of a light beam that is totally reflected at the interface between an optically denser medium with a refractive index n1 and an optically thinner medium with a refractive index n2 (n1>n2), if the angle of incidence of said light beam onto the interface exceeds the critical angle of total reflection. The critical angle is sin θ=n2/n1.

At the interface, the light beam escapes into and interacts with the optically thinner medium. Behind the reflecting surface a so-called evanescent wave is formed that has a penetration depth at the range of the wavelength. The penetration depth $d_p$ is dependent on the two refraction indexes $n_1$ and $n_2$ of the wavelength λ and the angle of incidence Θ that are used.

$$d_p = \frac{\lambda}{2\pi\sqrt{n_1^2\sin^2(\Theta) - n_2^2}}$$

If the optically thinner medium absorbs the incoming radiation, the totally reflecting beam is attenuated. The attenuation or partial extinction is dependent on the wavelength, and the spectrum of totally reflected radiation can be used for spectroscopic evaluation in analogy to transmission measurements. The composition of the optically thinner medium can be inferred from the transmission and/or extinction spectrum.

Furthermore, the determination of ingredients of low and very low concentrations based on the absorption of infrared radiation is a known method for detecting $CO_2$. It takes advantage of the fact that molecules are set into vibration by infrared radiation of selected wavelengths. Dissolved $CO_2$ has a characteristic absorption band in the range around 4.3 μm. Based on the Beer-Lambert law, absorption can be translated to precise concentration measurements. It describes:

$$E_\lambda = -lg(I/I_0) = \epsilon_\lambda \cdot c \cdot d, \text{ where:}$$

$E_\lambda$ is the absorption at wavelength λ,
I is the intensity of the transmitted light,
$I_0$ is the intensity of the incident light,
$\epsilon_\lambda$ is the extinction coefficient,
c is the concentration, and
d is the layer thickness of the radiated body.

For measuring the $CO_2$ content of fluids, the two basic principles are preferably utilized in combination.

FIG. 1 shows a prior art ATR sensor. The core piece of the ATR sensor is a reflection body which is transparent and has a high refractive index in the range of interest for the radiation employed, in particular IR radiation around 4.3 μm. Known, particularly crystalline, materials for such optical reflection bodies are, for example, sapphire, ZnSe, Ge, SI, thallium bromide, YAG, spinel, etc. Often the reflection body is designed in such a way that the intensity yield is increased by multiple reflections on its interior. Other sensor components are one or more radiation sources of adequate (ranges of) frequencies, optionally means for selecting frequencies, and one or more detectors for the reflected radiation; they, too, can be frequency-selective. An evaluation unit saves the intensities measured at the detector and supports the evaluation of the data and/or converts the measured intensities to the respective $CO_2$ concentrations. At least the sensor components are integrated inside a housing. In this housing, other required members are arranged as well, such as lines, seals, means of selecting frequencies, etc. The measurement face of the reflection body is contacted with the fluid to be measured.

In its simplest form, an ATR sensor comprises a reflection body formed by a crystal as an optically active element that allows for internal reflections, a source of radiation and a detector. With its measurement face, the reflection body protrudes into the fluid to be evaluated, either directly into the processing stream or into the fluid which is present in a container. Thus, such ATR sensors have at least three sensor components arranged in a mutually suitable manner. The optically active element, or the reflection body, is pressed against the housing in a gas-tight manner or connected to it in a pressure- or gas-tight manner, such as by means of an O-ring or inelastic seals, such as those made of PEEK (polyetheretherketone), TEFLON® (PTFE, polytetrafluoroethylene), etc.

It has been shown that such ATR sensors are flawed, in particular that there is a long-term drift with which the measured feedback values increasingly differ from the actual measured values. For this reason it has been necessary to calibrate and/or to readjust such measurement devices at regular, relatively brief intervals.

SUMMARY OF THE INVENTION

It is accordingly an object of the invention to provide a method and sensor which overcome the above-mentioned disadvantages of the heretofore-known devices and methods of this general type and which provide for a measurement method and an ATR sensor by which these drawbacks can be avoided. Inventive ATR sensors are supposed to be largely thermally stable in order to survive high-temperature cleaning procedures in operation, which sensors like this are subjected to in practice, particularly if they are used for measuring food products.

With the foregoing and other objects in view there is provided, in accordance with the invention, a method of measuring a $CO_2$ content in a fluid, the method which comprises:

providing an ATR sensor with a sensor housing defining an interior space and a plurality of sensor components disposed within the sensor housing, the sensor components including an electromagnetic radiation source for emitting in a predefined wavelength range, a reflection body permeable to radiation and contactable with the fluid to be evaluated, a detector for detecting reflected radiation, and additional elements for conducting the measurement and for operation;

prior to sealing the sensor housing of the ATR sensor, introducing $CO_2$ getter material into the sensor housing and/or into a receiving space of an additional housing communicating with the interior space of the sensor housing; and subsequently sealing the interior space and/or the receiving space in a gas-tight manner for avoiding a measurement value drift and for keeping radiation paths free of $CO_2$.

In a method of the type described above these objects are achieved by introducing $CO_2$ getter material into the housing and/or into the receiving space of an additional housing connected or connectable to the interior space of the housing before sealing the housing and/or the receiving space of the additional housing in a gas-tight manner, particularly for avoiding a measurement value drift and for keeping the radiation paths $CO_2$ free. An ATR sensor of the type mentioned above is characterized in that $CO_2$ getter material is contained in the interior space of the housing sealed in a gas-tight manner and/or in the receiving space of an additional housing connected or connectable to the interior space of the housing.

Thorough and lengthy evaluations for finding the cause of the long-term drift varying from sensor to sensor revealed that this long-term drift is mainly due to degassing $CO_2$ from the electric sensor components used and other members required for measuring, which are enclosed in the interior space of the housing. The $CO_2$ emerging from these sensor components and members affects the measurement directly, as it reaches the radiation path and affects the electromagnetic radiation that is lead from the source of radiation to the detector. As the members and sensor components present in the housing inevitably and continuously release low or very low amounts of $CO_2$, so far common practice included that measurement values differed, and the longer the sensor had been in use the more these values deviated from the set values originally adjusted or calibrated.

Now, with getter material included and/or enclosed in the housing, it is possible to decouple the gradually degassing $CO_2$ and thus keeping calibration of the ATR sensor at its exact initial value.

It is of advantage, if the $CO_2$ getter material is introduced in at least an amount that can receive $CO_2$ degassing from the sensor components and other components contained in the housing and/or in the additional housing over a period of time which corresponds at least the expected service life of the ATR sensor or at least the period of time until the opening of the housing and/or additional housing for required maintenance and/or readjusting purposes. Thus, a largely calibration-free and maintenance-free ATR sensor is produced. At predefined maintenance times, which are determined in particular by the replacement of the required seals, which age under process conditions, and optionally by the maintenance of the electrical and optical members, even the getter material can be replaced. According to the invention, a virtually drift-free $CO_2$ sensor is produced, which requires minimal maintenance effort over its entire service life.

It is of advantage if the $CO_2$ getter material takes up $CO_2$ internally and binds it upon heating, preferably to a temperature of 200 to 1000° C., preferably to 300 to 600° C., and thereby provides its surface for the uptake of further $CO_2$ molecules. Such porous getter material has the ability to internally take up the $CO_2$ molecules bound on its surface upon heating and can therefore absorb $CO_2$ upon temporary reactivation over the entire service life of the ATR sensor, thus repeatedly providing free surface areas for the uptake or attachment of new $CO_2$ molecules degassing from the sensor components and members that are present in the interior space.

It is useful if the $CO_2$ getter material is thermally stable up to 200° C., preferably 150° C., with respect to its $CO_2$ affinity. In case the device requires cleaning during use, carried out at the specified temperatures, or during high-temperature measurements, the getter material remains active.

The sensor can have a directly integrated control and evaluation unit or a transducer with an individual unit for display and operation of the sensor, such as a PC or display and control devices, for example. Via interfaces, multiple sensors can be monitored at the same time, and their data read and used for process control.

It can be of advantage, if, in addition to the $CO_2$ getter material, other getter materials that bind and/or absorb carbonaceous gases and/or steam are placed in the interior space of the housing and/or the receiving space of the additional housing. This way, any influence from other gas molecules can be ruled out.

It can be of advantage in terms of construction, if a connector for a purging gas line is formed at the housing and/or additional housing.

Basically it is also possible that the $CO_2$ getter material is included in the receiving space of an additional housing, which is optionally connected to the interior space of the housing via a line that can be plugged by a plugging unit, and/or that a device for forced circulation, preferably a ventilator, of the atmosphere present in the interior space and/or in the receiving space is arranged in the interior space of the housing and/or in the receiving space. It can also be useful, if a wall opening that can be sealed in a gas-tight manner is formed in the housing and/or in the additional housing for replacing or refilling $CO_2$ getter material.

In order to increase the service life and capacity of the getter material, it can be intended for a heating device for the $CO_2$ getter material to be provided for activating or reactivating the $CO_2$ getter material in the housing and/or in the additional housing.

Other features which are considered as characteristic for the invention are set forth in the appended claims.

Although the invention is illustrated and described herein as embodied in a method and sensor for measuring a $CO_2$ content of a fluid, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

Figure 1:
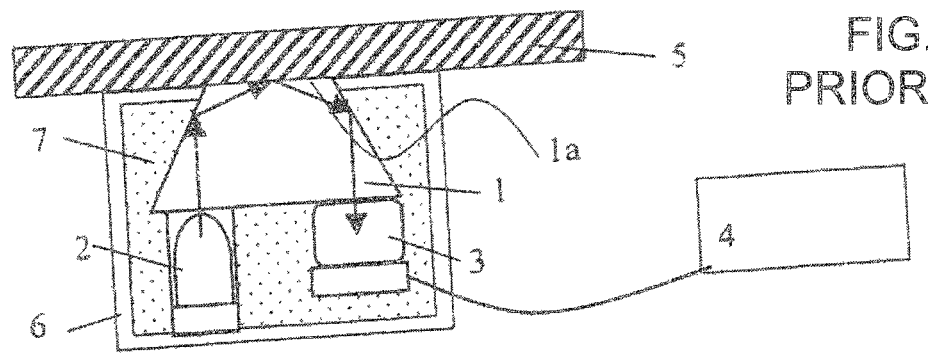
FIG. 1 is a diagrammatic view of a prior art ATR sensor.
Figure 2:
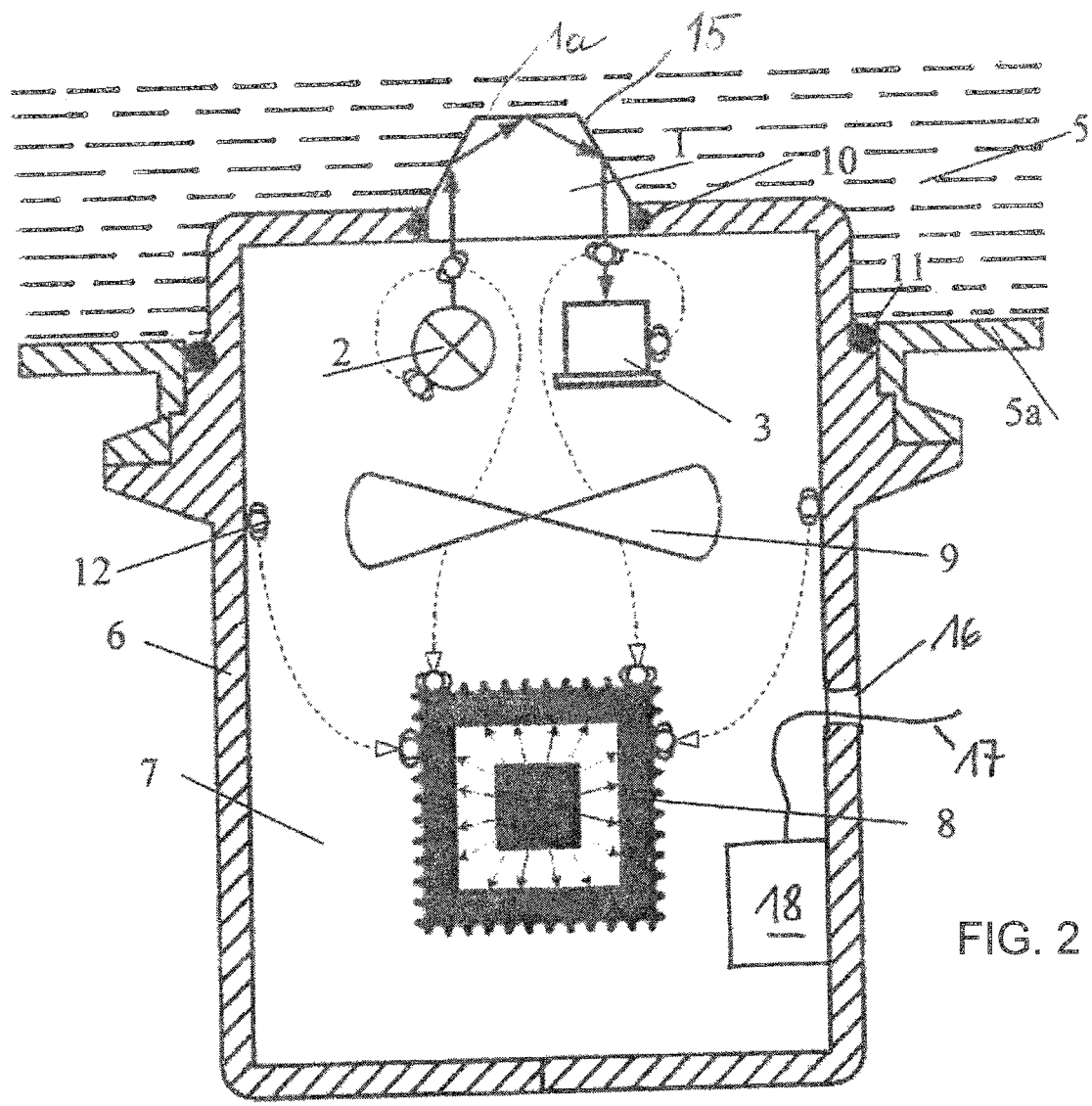
FIG. 2 shows an ATR sensor according to the invention.
Figure 3:
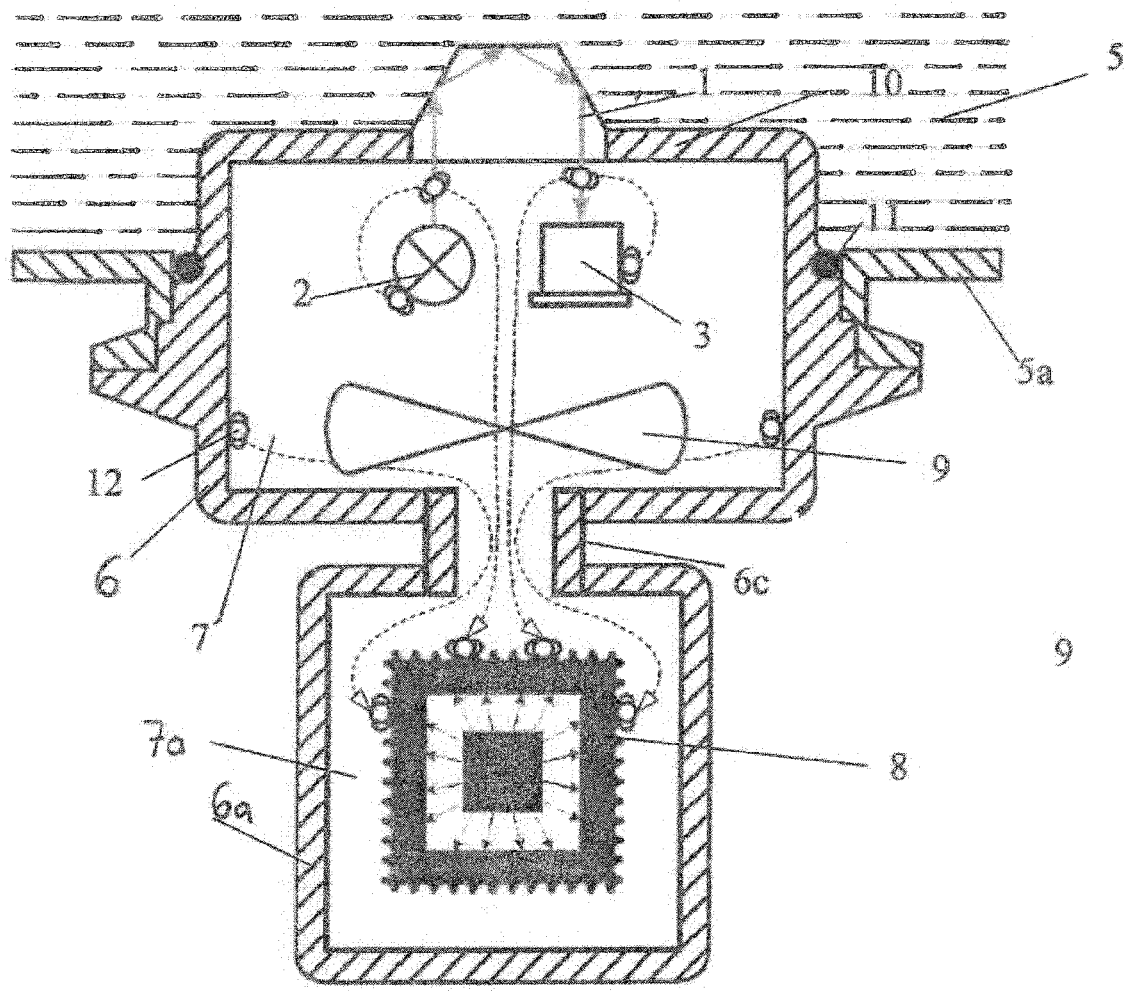
FIG. 3 shows an embodiment of an ATR sensor according to the invention with the getter material in a receiving space connected to the interior.
Figure 4:
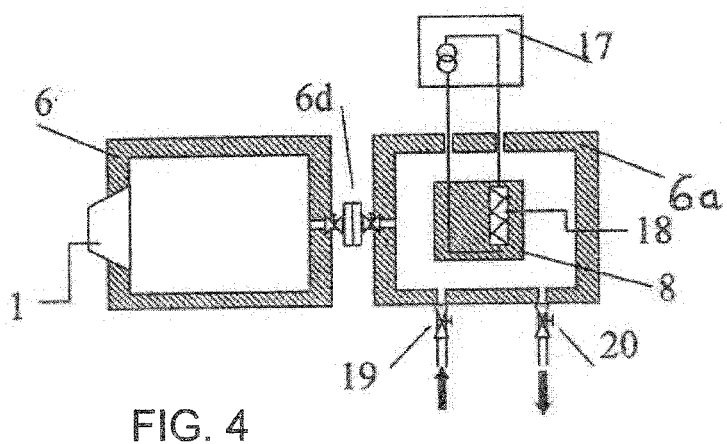
FIG. 4 shows an embodiment of an ATR sensor with the getter material located in a receiving space of an additional housing.

Referring now to the figures of the drawing in detail, FIG. 2 shows an ATR sensor that is constructed in a similar way as the one depicted in FIG. 1, in which getter material is present in the interior space of the housing. FIG. 3 shows an embodiment of an ATR sensor according to the invention, in which the getter material is found in a receiving space connected to the interior space of the housing. FIG. 4 shows an embodiment of an ATR sensor, in which the getter material is located in an individual receiving space of an additional housing connectable to the interior space of the housing and equipped with a heating device.

FIG. 2 shows an embodiment of an ATR sensor, in which an ATR element, i.e. a reflection body 1 formed by a crystal, is arranged within a sensor housing 6. The sensor housing 6 is inserted into a line 5a for a fluid 5 with an exterior wall 10 with seals 11. An electromagnetic source of radiation 2 emits electromagnetic radiation to the reflection body 1 at a predefined wavelength range, which, following multiple reflection at the interfaces 15 of the reflection body 1 is reflected to the fluid 5 to be evaluated in a detector 3. The fluid 5 to be evaluated can be routed in a line 5a, or it is arranged in a container. Precautions have to be taken for the reflection body 1 being in respective contact with the fluid 5 to be evaluated, in particular liquids. In the interior space 7 of the housing 6, apart from the sensor components indispensable for measuring all other members required for carrying out the measurement are found, which are indicated by 18. In the interior space 7 of the housing 6 the getter material 8 is present. Means of moving the internal atmosphere, such as a ventilator 9, can also be provided in the interior space 7, which supply the getter material with the $CO_2$ molecules 12 emerging from the sensor components and other members of the interior space 7 but also with those emerging from the means themselves. Once a $CO_2$ molecule hits the surface of the getter material 8, it is bound.

The housing 6 of the ATR sensor is configured in such a way that leak rates are minimized compared to the environment and the exterior spaces as well as to the fluid 5 to be evaluated. This is accomplished by an entirely closed housing 6 and by vacuum-tight passages and/or seals 16 for any lines 17. In addition, the electrical connections and the seat of the reflection body 1 are carried out in a manner stable towards pressure and temperature with respect to the process environment. The housing 6 can be designed specifically resistant against chemicals for particular uses.

The getter material 8 is preferably selected to have as little activation energy as possible. The getter material 8 is a chemically reactive material that can bind $CO_2$ at its surface either by absorbance or by chemical binding. It is of advantage, if the $CO_2$ molecules precipitated on the free surfaces can be removed from the surface by heating in a way that they penetrate the interior of the getter material 8, whereby space is created again on said surface for binding further $CO_2$ molecules, thus enabling reactivation of the getter material 8.

In order to be able to utilize such getter materials 8 advantageously in inventive ATR sensors, the getter material 8 is placed in the interior space 7, which has a surface of sufficient size to be able to bind all $CO_2$ molecules degassing during a predefined operation period. Alternatively, it can be taken into account to use getter material 8 which can be regenerated by heating up. It is also possible that, by supplying a purging gas, the getter material 8 is purged and the $CO_2$ molecules emerging thereby are eliminated. This purging is preferably carried out at an increased temperature of the getter material 8.

Suitable getter materials 8 include, for example, barium, aluminum and/or magnesium alloys; titanium and platinum are also suitable for this purpose. Non-evaporable getter materials 8 can also be utilized, such as, for example, those known from vacuum engineering. Together with $CO_2$ they form stable compounds, and even at increased temperatures, absorbed $CO_2$ molecules are not released by the getter material. Zirconium is an example of such getter materials 8.

As shown in FIG. 3, it is also possible to connect the interior space 7 of the housing to the interior, or receiving, space 7a of an additional housing 6a and to place the getter material 8 or other getter material 8 in the receiving space 7a. The atmosphere of the interior space 7 is interchanged with the atmosphere of the receiving space 7a via a ventilator 9, and the $CO_2$ molecules degassed from the interior space 7 of the housing are transported to the getter material 8. The additional housing 6a can be designed to be removable and/or to be connectable to the housing 6 in a gas-tight manner, such as, for example, via a blocking device 6d disposed in the connecting line 6c, as shown in FIG. 4.

If $CO_2$ molecules that have been absorbed form a protecting passivation layer at the gettering surface, the getter material 8 can be reactivated by heating up after a predefined period. Depending on the material, the activation temperature can be 200 to 1000° C. Upon activation, the $CO_2$ molecules and molecule compounds bound to the getter surface due to the temperature increase are mobilized and diffused into the getter volume, whereby the surface becomes absorptive again. Such activation of the getter material 8 could also occur during cleaning of the exterior surface of the housing 6 in operation at the designed increased cleaning temperature or by an individual heating device 18, which is arranged in the interior space 7 of the housing 6 or in the receiving space 7a of the additional housing 6a. The heating device 18 is supplied and controlled by a power source and a control unit 17, respectively.

As illustrated in FIG. 4, purging gas can be supplied to the housing 6 and/or the additional housing 6a via a purging gas inlet 19 and a purging gas outlet 20.

The invention claimed is:

1. A method of measuring a $CO_2$ content in a fluid, the method which comprises:
    providing an ATR sensor with a sensor housing defining an interior space and a plurality of sensor components disposed within the sensor housing, the sensor components including an electromagnetic radiation source for emitting in a predefined wavelength range, a reflection body permeable to radiation and contactable with the fluid to be evaluated, a detector for detecting reflected radiation, and additional elements for conducting the measurement and for operation;
    prior to sealing the sensor housing of the ATR sensor, introducing $CO_2$ getter material into at least one element selected from the group consisting of the sensor housing and a receiving space of an additional housing communicating with the interior space of the sensor housing; and
    subsequently sealing at least one space selected from the group consisting of the interior space and the receiving space in a gas-tight manner;

wherein the introducing step comprises introducing the $CO_2$ getter material at least in an amount that can take up $CO_2$ degassing from the sensor components and other components contained in the sensor housing or the additional housing over a period of time which corresponds at least to an expected service life of the ATR sensor or at least to a period until at least one housing selected from the group consisting of the sensor housing and the additional housing is opened for at least one purpose selected from the group consisting of required maintenance and adjustment purposes.

2. The method according to claim 1, which comprises sealing the housing for avoiding a measurement value drift and for keeping radiation paths free of $CO_2$.

3. An ATR sensor, comprising:
a sensor housing defining an interior space;
a plurality of sensor components in said sensor housing, said sensor components including an electromagnetic source of radiation for emitting a predefined wavelength range, a reflection body permeable to radiation and contactable with a fluid to be evaluated, and a detector for reflected radiation, and other members for conducting a measurement and for operation;
an amount of $CO_2$ getter material disposed in at least one space selected from the group consisting of said interior space of said housing sealed in a gas-tight manner and a receiving space of an additional housing connected or connectable to communicate with said interior space in a gas-tight manner;
wherein the amount of $CO_2$ getter material is at least an amount that can take up $CO_2$ degassing from said plurality of sensor components and other components contained in said sensor housing or said additional housing over a period of time which corresponds at least to an expected service life of the ATR sensor or at least to a period until at least one housing selected from the group consisting of said sensor housing and said additional housing is opened for at least one purpose selected from the group consisting of required maintenance and adjustment purposes.

4. The ATR sensor according to claim 3, configured for measuring a $CO_2$ content in a fluids.

5. The ATR sensor according to claim 3, wherein said $CO_2$ getter material is configured to take up $CO_2$ internally and to bind the $CO_2$ upon heating, providing a surface for receiving further $CO_2$ molecules.

6. The ATR sensor according to claim 5, wherein said $CO_2$ getter material is configured to take up and to bind $CO_2$ upon heating to a temperature between 200 and 1000° C.

7. The ATR sensor according to claim 5, wherein said $CO_2$ getter material is configured to take up and to bind $CO_2$ upon heating to a temperature between 300 and 600° C.

8. The ATR sensor according to claim 5, wherein said $CO_2$ getter material is thermally stable in terms of a $CO_2$ affinity up to 200° C.

9. The ATR sensor according to claim 5, wherein said $CO_2$ getter material is thermally stable in terms of a $CO_2$ affinity up to 150° C.

10. The ATR sensor according to claim 3, wherein said other members for conducting a measurement and for operation are elements selected from the group consisting of control units, evaluation units, control and evaluation units, transducer seals, lines, receiving containers for said $CO_2$ getter material, and electronic members disposed in at least one space selected from the group consisting of said interior space and said receiving space.

11. The ATR sensor according to claim 3, which comprises further getter materials, in addition to said $CO_2$ getter material, disposed in at least one space selected from the group consisting of said interior space of said housing and in said receiving space of said additional housing for at least one purpose selected from the group consisting of binding absorbing carbonaceous gases, absorbing carbonaceous gases, binding steam, and absorbing steam.

12. The ATR sensor according to claim 3, which comprises a connector for a purging gas line, or a purging gas line, connected to at least one housing selected from the group consisting of said sensor housing and said additional housing.

13. The ATR sensor according to claim 3, wherein said $CO_2$ getter material is introduced into a receiving space of the additional housing, which is connected to said interior space of said housing via a line equipped with an optional plugging unit.

14. The ATR sensor according to claim 3, which comprises a device for forced circulation of an atmosphere present in at least one space selected from the group consisting of said interior space and said receiving space, said device disposed in at least one space selected from the group consisting of said interior space of said housing and in said receiving space.

15. The ATR sensor according to claim 14, wherein said device for forced circulation is a ventilator.

16. The ATR sensor according to claim 3, which comprises a wall opening that can be sealed in a gas-tight manner formed in at least one housing selected from the group consisting of said housing and said additional housing for replacing or refilling $CO_2$ getter material.

17. The ATR sensor according to claim 3, which comprises a heating device for heating said $CO_2$ getter material within at least one housing selected from the group consisting of said housing and said additional housing for activating or reactivating said $CO_2$ getter material.

* * * * *